United States Patent [19]
Amit et al.

[11] Patent Number: 5,186,627
[45] Date of Patent: Feb. 16, 1993

[54] HAND-ACTUATED ROTATABLE TOOTHBRUSH

[76] Inventors: Noah Amit, 49 W. 44th St., New York, N.Y. 10026; Miro S. Cater, 193 Hattertown Rd., Newtown, Conn. 06470

[21] Appl. No.: 800,515

[22] Filed: Dec. 3, 1991

Related U.S. Application Data

[63] Continuation-in-part of Ser. No. 694,468, May 1, 1991.

[51] Int. Cl.$^5$ .................. A61C 17/32; A46B 13/08
[52] U.S. Cl. .................. 433/216; 15/22.1; 15/28; 134/6
[58] Field of Search .............. 15/22.1, 22.2, 22.4, 15/28, 27; 128/62 A; 433/216; 134/6

[56] References Cited

U.S. PATENT DOCUMENTS

| | | |
|---|---|---|
| 1,212,001 | 1/1917 | Baxter . |
| 1,265,536 | 5/1918 | Sharps . |
| 1,557,244 | 10/1925 | Dominque ................ 15/28 |
| 1,620,330 | 3/1927 | Douglass . |
| 1,947,324 | 2/1934 | Zerbee ................ 15/28 |
| 2,660,745 | 12/1953 | Yusko ................ 15/22.1 |
| 4,048,690 | 9/1977 | Wolfson ................ 15/22.1 |
| 4,156,620 | 5/1979 | Clemens ................ 15/22.1 |
| 4,274,173 | 6/1981 | Cohen ................ 15/28 |
| 4,545,087 | 10/1985 | Nahum ................ 15/22.1 |
| 5,068,939 | 12/1991 | Holland ................ 15/22.1 |
| 5,070,567 | 12/1991 | Holland ................ 15/28 |

FOREIGN PATENT DOCUMENTS

1300138  6/1962  France ................ 15/27

Primary Examiner—Edward L. Roberts

[57] ABSTRACT

A hand powered rotatable toothbrush is characterized by elements, such as tufts of brush bristles, positionally fixed to the brush head to frictionally engage tooth surfaces and thereby positionally stabilize the brush head so that a distal portion of the brush handle can be longitudinally reciprocated relative to the brush head. One or more rotatable brush members mounted on the brush head are operatively connected to the distal handle portion, as by a rack and pinion, to cause the brush members to be rotated in response to longitudinal handle reciprocation. In one embodiment the rotatable brush member cyclically rotates in opposite directions in response to back and forth linear motion of the handle. In another embodiment the rotation of the brush member is in the same direction, irrespective of the direction in which the handle moves.

47 Claims, 6 Drawing Sheets

HAND-ACTUATED ROTATABLE TOOTHBRUSH

CROSS-REFERENCE TO RELATED APPLICATIONS

This is a continuation-in-part of U.S. patent application Ser. No. 07/694,468, filed May 1, 1991 by Noah Amit and entitled "Method and Apparatus for Brushing Teeth with Cyclically Rotating Brush Strokes".

BACKGROUND OF THE INVENTION

1. Technical Field

The present invention relates to improvements in methods and apparatus for brushing teeth and, more particularly, to toothbrushes having bristles that are rotatable relative to the brush head in response to linear reciprocation of the brush handle.

2. Discussion of the Prior Art

It has long been recognized to be advantageous to apply a rotary brushing action to teeth for the purpose of removing deposits that build up on tooth surfaces, particularly adjacent the gumline. The desired brush rotation is about an axis perpendicular to the tooth surface and, for the usual toothbrush configuration, is approximately perpendicular to the brush handle. The hand manipulation required of a conventional toothbrush to effect this desirable rotary brushing action is difficult at best, particularly in view of the small surface area to be cleaned and the small radius of movements of the hand required to accomplish the necessary brush strokes. Powered toothbrushes have been employed to accomplish the desirable rotary brush action but have achieved only, limited commercial success, primarily because of the reluctance by many consumers to place a powered implement in their mouths. Examples of such powered toothbrushes for effecting rotary brush action of the type describe are found in U.S. Pat. Nos. 1,265,536 (Sharps), 1,947,324 (Zerbee), 4,156,620 (Clemens), 4,274,173 (Cohen), 4,827,550 (Graham et al) and 4,845,795 (Crawford et al).

In point of fact, consumers are most comfortable with nonpowered toothbrushes requiring longitudinal reciprocation of the handle to effect brushing. The present invention is concerned with providing an efficient and inexpensive non-powered (i.e., operated solely in response to movement of the user's hand) technique for converting longitudinal brush handle reciprocation to the desired rotational brush strokes. There have been a number of commercially unsuccessful attempts to accomplish this desirable result. For example, in U.S. Pat. No. 1,557,244 (Domingue) there is disclosed a plurality of brush elements, each including plural tufts, mounted in a brush head by means of toothed pinions that are caused to rotate by longitudinal reciprocation of a rack secured to the brush handle and extending into the brush head. However, in order to use this brush, the brush head must be held stationary with one hand while the handle is reciprocated with the other hand. Such two-handed operation has not achieved acceptance among consumers, most likely because of the difficulty involved in holding the brush head stationary while cleaning teeth located in the back and sides of the mouth.

Although the apparatus disclosed in the aforementioned U.S. Pat. No. 4,156,620 (Clemens) is a powered toothbrush, it is of background interest for the present invention because of its disclosure of a power driven rack that is longitudinally reciprocable to cyclically rotate a plurality of single tuft brush elements. Each tuft is controllably rotated about its central axis at a speed of approximately three thousand revolutions per minute. Since each brush element is a single tuft rotated about the central tuft axis, the individual bristles are caused to alternately twist in helical fashion and then release in a manner described by Clemens as essential in providing the desired tooth cleaning action. In addition, the single tuft elements of the Clemens device are rotated for equal numbers of revolutions in opposite directions during each cycle. The high speed, multiple revolution, twisting operation results from the power driven nature of the device. As noted above, consumers are most comfortable with nonpowered toothbrushes.

In U.S. Pat. No. 1,620,330 (Douglass), there is a disclosure of plural brush sections symmetrically disposed about respective axes and mounted on the brush head to be freely rotatable about those axes relative to the head. However, there is no mechanism provided for positively rotating the brushes in response to longitudinal reciprocation of the brush handle. In fact, true longitudinal movement of the brush handle creates purely radial, as opposed to tangential, net forces on the rotatable brush sections so that there is no turning force applied thereto. Accordingly, in the absence of some mechanism for positively converting the longitudinal forces to rotational forces, there is negligible rotation of the symmetrically mounted brush sections.

In U.S. Pat. No. 1,212,001 (Baxter) there is disclosed a toothbrush having plural brush sections mounted eccentrically on the brush head for pivotability between stops about respective axes. Once again, there is no positive mechanism for rotating the brush sections; rather, the frictional engagement between the ends of the bristles and the surfaces of the teeth provides the force for effecting pivoting of the brush sections during the initial portion of each linear stroke of the brush handle. While that pivoting action is taking place, the bristle ends flex but move very little, if at all, across the teeth. It is only after the brush sections reach the pivot stop members that the bristles move across the teeth, and such movement is linear, in the direction of handle movement, not rotational. Therefore, although the brush sections pivot with each change in handle direction, the bristles do not apply the desired rotary brush strokes to the teeth.

There are other prior art toothbrushes wherein longitudinal movement of the brush handle is intended to be converted into some other degree of motion in the brush itself. For example, U.S. Pat. No. 2,660,745 (Yusko) discloses a toothbrush wherein the entire brush head oscillates about the longitudinal axis of the handle in response to longitudinal reciprocation of the handle. The result is an up and down movement of the brush bristles across the surfaces of the teeth. This brushing action was, at one time, considered to be efficient but in recent years has fallen into disfavor among dental professionals.

Still other toothbrushes having bristles that move in relation to the handle or head are found in the following U.S. Pat. Nos.:

| U.S. Pat. No. | Patentee |
| --- | --- |
| 618,690 | Ter Laag |
| 1,257,883 | Kone |
| 1,911,973 | Ruse |
| 2,160,836 | Davids |

| U.S. Pat. No. | Patentee |
| --- | --- |
| 2,184,850 | Schloss |
| 2,188,449 | Stewart |
| 2,290,454 | Steinberg |
| 2,411,610 | Aaron |
| 2,799,878 | Brausch |
| 2,917,759 | Siampaus |
| 3,110,918 | Tate, Jr. |
| 3,214,776 | Bercovitz |
| 3,994,039 | Hadary |
| 4,638,520 | Eickmann |
| 4,682,584 | Pose |
| 4,766,630 | Hegemann |

These patents all disclose devices having different brush action than the desirable rotary action described above, but are of general interest in that they show a wide variety of actuating mechanisms for achieving brush movement.

OBJECTS AND SUMMARY OF THE INVENTION

It is therefore a primary object of the present invention to provide a toothbrush having a built-in mechanism for positively converting reciprocating linear motion of the brush handle to rotational movement of one or more brush elements relative to the It is another object of the present invention to provide an improved method and apparatus for applying rotational brush strokes to teeth in response to linear reciprocation of the brush handle, the brush stroke rotation being about an axis oriented perpendicular to the handle reciprocation direction.

It is still another object of the present invention to positively convert linear reciprocation of a toothbrush handle to oscillatory rotation of one or more brush sections about respective axes oriented perpendicular to the handle without relying on frictional engagement of the rotary brush section bristles with surfaces of the teeth in order to effect the conversion.

A further object of the invention is to provide an improved method and apparatus for positively converting reciprocating linear motion of a toothbrush handle to rotational movement of a brush element. Depending upon the embodiment the brush element rotation may either change directions with changes in handle direction or be in the same direction irrespective of brush handle direction.

It is also an object of the present invention to provide a toothbrush requiring a minimal number of easily assembled parts while retaining the capability of positively converting linear reciprocation of the brush handle to rotation of a brush element mounted on the brush head.

An additional object of the present invention is to provide a rotary toothbrush in which plural rotary brush elements mounted on the brush head are positively rotated in response to linear reciprocation of the brush handle.

In accordance with the present invention, the aforementioned desired rotary brushing action in a toothbrush is achieved using at least one rotatable brush section and at least one positionally fixed brush section mounted on a toothbrush head so that all of the bristles face in the same general direction, typically perpendicular to the length dimension of the brush handle. The rotatable section is positively rotated in response to longitudinal reciprocation of the handle by means of a rack and pinion, or other equivalent mechanism. Plural rotatable brush sections may be disposed in two lines along opposite longitudinal edges of the brush head, or in a single line along the longitudinal center of the brush head, or in any other regular or irregular pattern. Importantly, the fixed brush section serves to positionally stabilize the brush head by frictionally engaging the teeth, thereby assuring that the longitudinal reciprocation of the handle is positively converted to rotation of the rotatable brush section. The bristles of the rotatable brush section may be shorter than, or otherwise recessed relative to, the fixed brush section; as a consequence, in response to longitudinal forces exerted on the brush head, the fixed brush bristles flex while frictionally engaging the tooth surfaces as the bristles of the rotatable section are brought into direct contact with the tooth surfaces to be brushed. The fixed bristles may be replaced with other structure projecting from the brush head and capable of frictionally engaging tooth surfaces to stabilize the brush head.

In one embodiment of the invention the rotatable brush section includes a pinion engaged by a rack defined on the brush handle to cause the rotatable brush section to rotate in alternate directions as the longitudinal direction of the handle alternates. In an alternate embodiment the brush handle carries two racks disposed on opposite sides of the pinion in a manner such that the racks alternately engage the pinion as the longitudinal direction of the handle changes. The consequence of being alternately driven by the two opposite racks is that the rotatable brush section rotates in only one direction irrespective of handle direction. In both embodiments, the entire brush can be easily assembled from only four parts, namely: a rotatable brush section, a base on which the rotatable brush section and fixed brush sections are mounted; a cover for the brush head; and a handle. The handle is capable of linearly reciprocating in the cover relative to the base to rotatably drive the rotatable brush section.

BRIEF DESCRIPTION OF THE DRAWINGS

The above and still further objects, features and advantages of the present invention will become apparent upon consideration of the following detailed description of the specific embodiments thereof, particularly when taken in conjunction with the accompanying drawings wherein like reference numerals in the various figures are utilized to designate like components, and wherein.

DESCRIPTION OF THE PREFERRED EMBODIMENTS

Referring specifically to FIGS. 1-5 of the accompanying drawings, a toothbrush includes four assembled parts, namely: a handle 10; a base 20; a rotatable brush member 30; and a cover 40. Base 20, rotatable brush member 30 and cover 40 comprise the toothbrush head. Handle 10 has a conventional proximal end and a shaft 11 and is provided with a flat apertured distal end portion 12. The aperture in portion 12 takes the form of a generally rectangular slot 13 defined entirely through the thickness dimension of portion 12. Slot 13 is enclosed on all four sides and has its longer sides extending in the length dimension of the handle. One of the longer sides of slot 13 has a row of regularly spaced tooth-like projections extending along substantially its entire length to define a toothed longitudinal rack 14 facing inwardly of slot 13. Distal portion 12 is somewhat wider than the rest of handle 10 and is provided with four chamfered exterior corners 15. The angle of the chamfered corners 15 is typically between fifty and sixty-five degrees to the longitudinal dimension of the brush, and the edges of the chamfer cuts may be rounded, if desired. The length of slot 13 is typically between seventy-five to ninety percent of the length of distal portion 12, and the length of rack 14 is typically between sixty and eighty percent of the slot length. The width of slot 13 is typically between fifty-five and seventy-five percent of the width of distal portion 12. The individual teeth of rack 14 typically extend into slot 13 approximately ten to fifteen percent of the slot width.

Figures 1, 2:
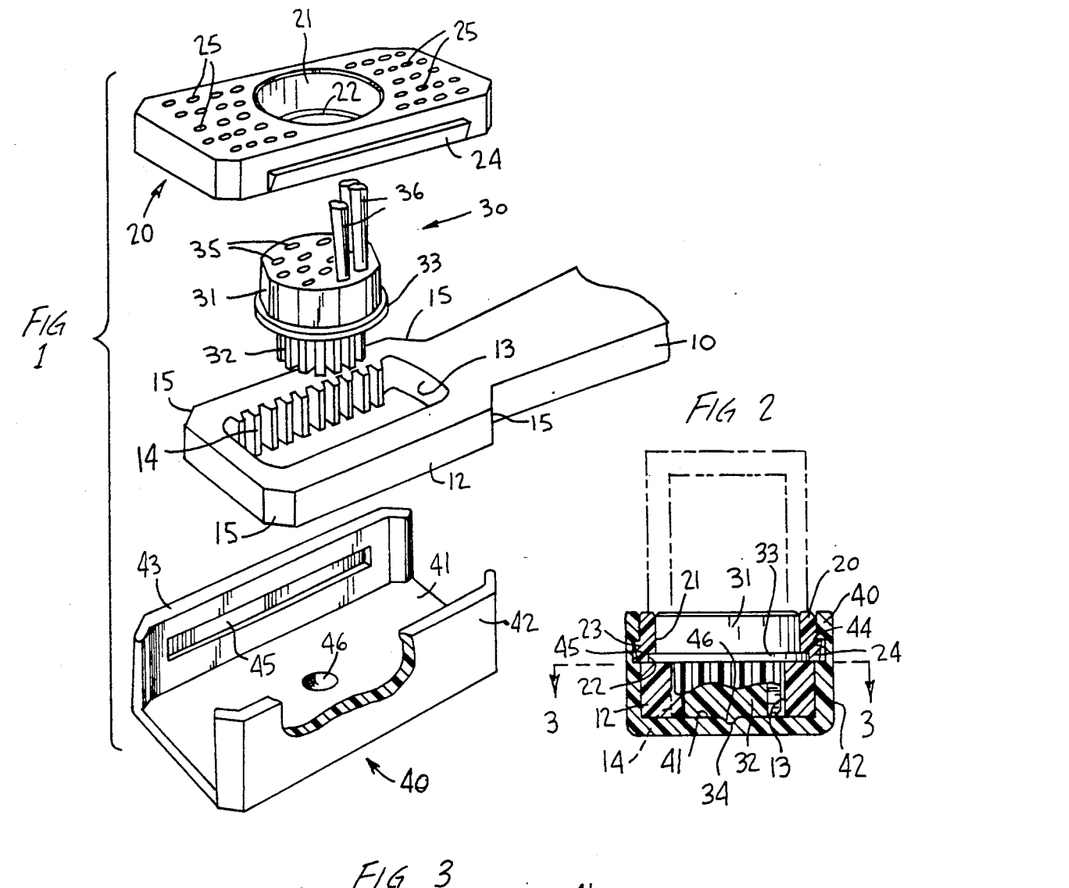
FIG. 1 is an exploded view in perspective of the head and forward portion of the handle of a toothbrush constructed in accordance with the principles of the present invention.
FIG. 2 is an elevational view in partial section of the toothbrush head of FIG. 1, taken along lines 2—2 of FIG. 4.

Base 20 is a generally rectangular plate member having width and depth dimensions substantially the same as those of distal portion 12 of handle 10. The length of base 20, however, is significantly greater than the length of portion 12. Typically, the length of distal portion 12 of the handle is between fifty and seventy percent of the length of base 20. The outside corners of base 20 are chamfered at the same angle as the chamfered corners 15 of distal portion 12 of the handle. A cylindrical hole 21 is defined entirely through the thickness of base 20 at a location substantially central of both the length and width dimensions. Throughout most of its axial length hole 21 has a first diameter. A very short segment 22 of hole 21, terminating at the back surface of base 20, has a slightly larger diameter. The transition between segment 22 and the rest of hole 21 is an annular shoulder facing toward the rear of base 20.

A pair of lateral projections 23, 24 extend along opposite longitudinal sides of base 20. Each projection 23, 24 extends outwardly from its respective base side at a location intermediate the front and rear surfaces of the base. More particularly, each projection includes a forwardly facing surface or ledge extending perpendicularly from the base side wall, the surface having a transverse dimension typically on the order of approximately five percent of the width dimension of base 20. From this surface projections 23 and 24 taper inwardly and rearwardly to intersect the rear surface of the base. The length of projections 23, 24 along their respective base sides is typically between sixty and eighty percent of the length of base 20.

The rear surface of base 20 is generally flat and is interrupted only by the widened segment 22 of hole 21. The front surface of the base has multiple holes 25 defined partway into the base depth. Holes 25 are disposed in two clusters, one cluster positioned forwardly of hole 21, the other positioned rearwardly of that hole. Each hole 25 has the bottom of a tuft 26 of brush bristles secured therein by a suitable adhesive. Tufts 26 are thus fixedly positioned in their respective holes 25 to extend perpendicularly from the front surface of base 20. Typically, there are between forty and sixty stationary tufts 26 secured in respective holes 25 in the front surface of the base 20.

Rotatable brush 30 includes a forward tuft supporting section 31, a rear pinion section 32 and an intermediate annular ledge 33 disposed axially between sections 31 and 32. Tuft supporting section 31 may be a cylinder or right polyhedron having a diameter slightly smaller than the diameter of hole 21 in base 20. The axial length of section 31 corresponds substantially to the axial length of the portion of hole 21 disposed between the front surface of base 20 and hole segment 22. Annular ledge 33 projects radially outward to a diameter slightly smaller than the diameter of hole segment 22 and has an axial length substantially corresponding to the axial length of hole segment 22. The dimensions of section 31 and ledge 33 ar such to permit the rotatable brush 30 to rotate in hole 21 about the central longitudinal axes of the hole and brush 30. In this regard, brush 30 is placed in base 20 by inserting section 31 into hole 21 from the rear of the base until ledge 33 abuts the annular shoulder between hole segment 22 and the rest of hole 21. Thusly placed, the front surface of section 31 is substantially flush with the front surface of base 20, and the rear surface of annular ledge 33 is substantially flush with the rear surface of base 20. In this position of the rotatable brush 30, pinion section 32 projects rearwardly from base 20.

Figure 3:
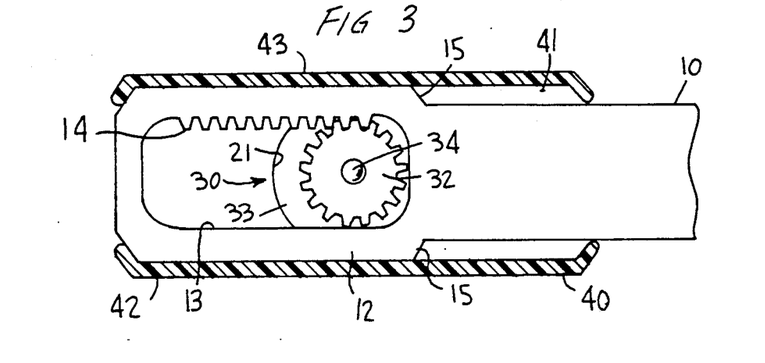
FIG. 3 is a plan view in partial section taken along lines 3—3 of FIG. 2.
Figure 4:
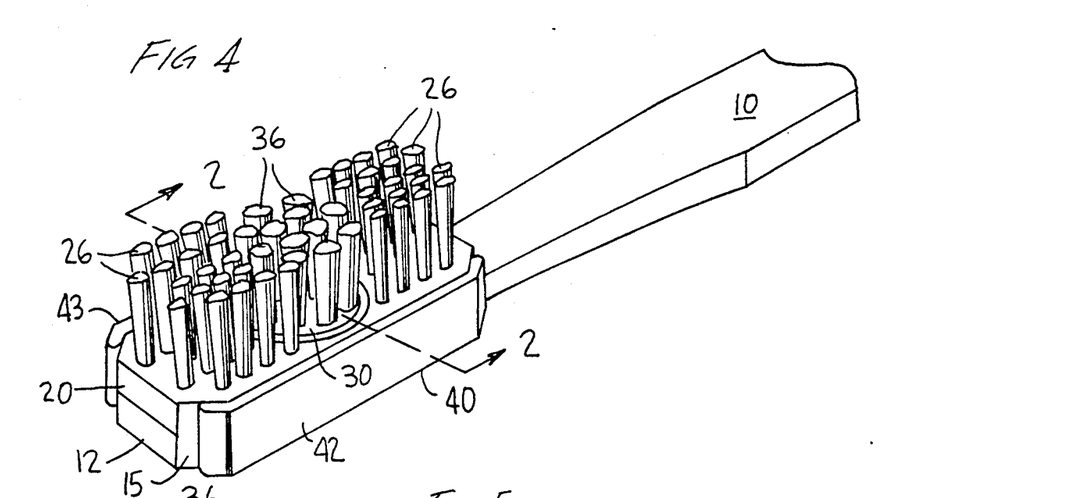
FIG. 4 is a view in perspective of the assembled toothbrush of FIG. 1.
Figure 5:
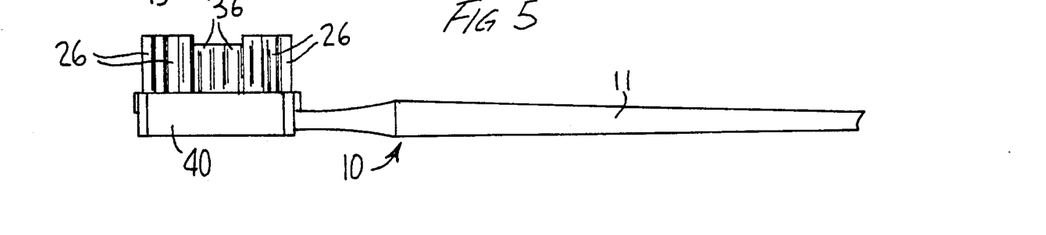
FIG. 5 is a side view in elevation of the toothbrush of FIG. 4.
Figure 6:
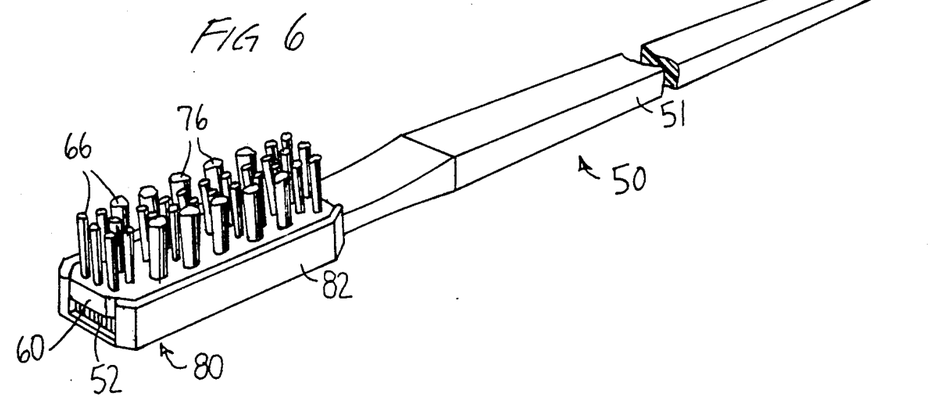
FIG. 6 is a view in perspective of a second embodiment of a toothbrush constructed in accordance with the principles of the present invention.
Figure 7:
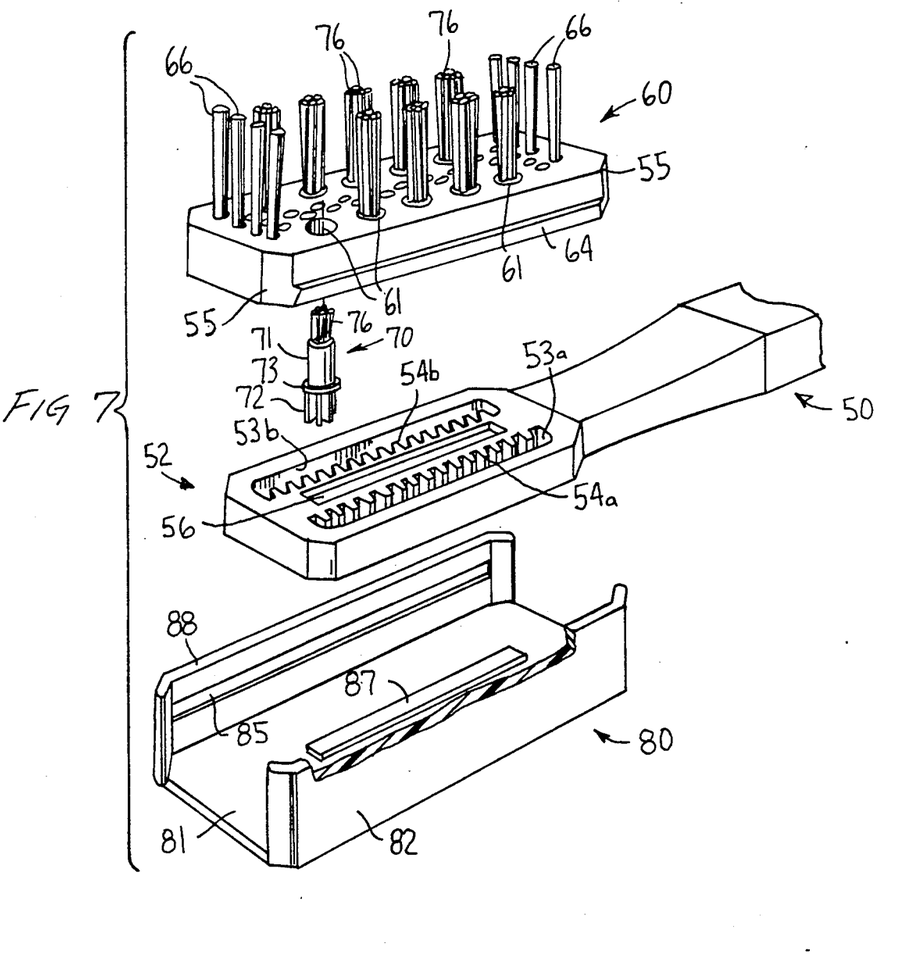
FIG. 7 is an exploded view in perspective of the toothbrush illustrated in FIG. 6.
Figure 8:
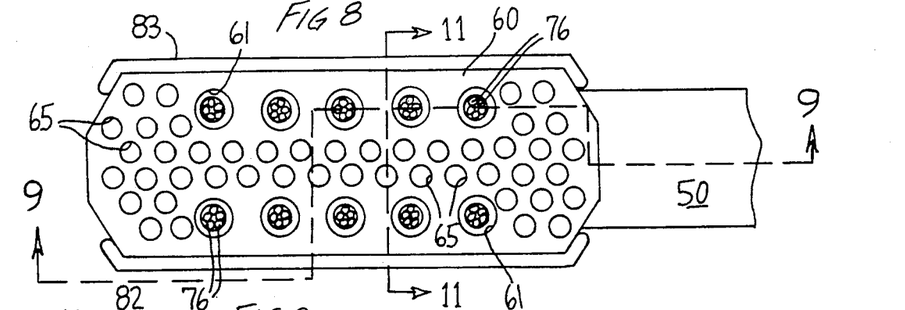
FIG. 8 is a top view in plan of the toothbrush illustrated in FIG. 6.
Figure 9:
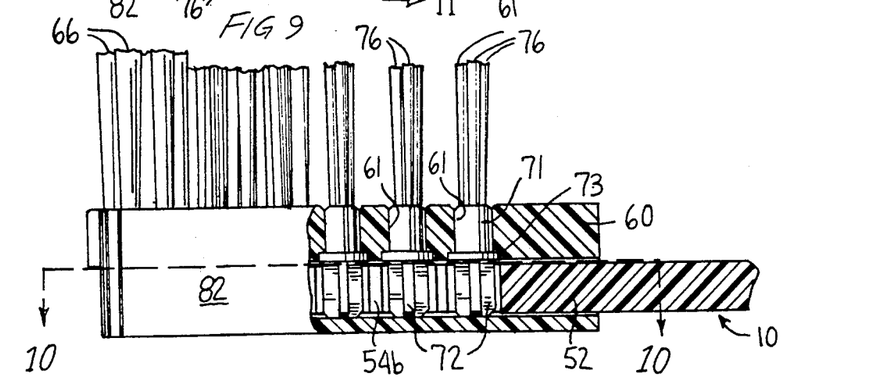
FIG. 9 is a side elevation view in partial section taken along lines 9—9 of FIG. 8.
Figure 10:
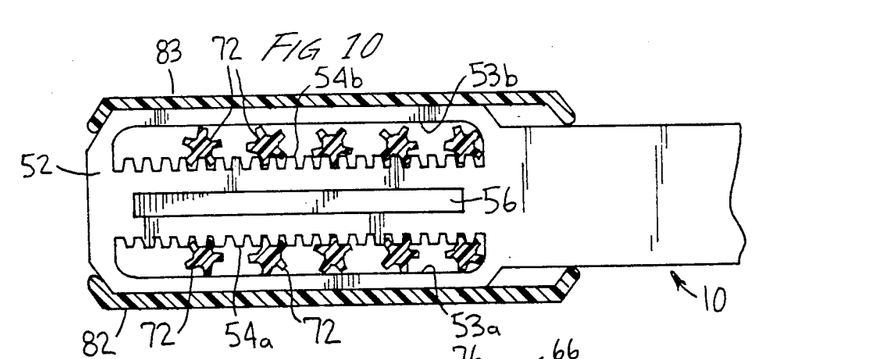
FIG. 10 is a view in section taken along lines 10—10 of FIG. 9.
Figure 11:
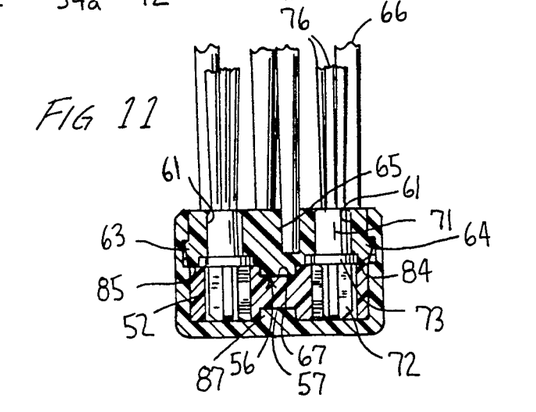
FIG. 11 is a view in section taken along lines 11—11 of FIG. 8.

Pinion section 32 is coaxial with section 31 and ledge 33 and has its radially extending teeth configured to mesh with the teeth in rack 14 in cooperative relation. Specifically, when the toothbrush is assembled, the front surface of distal portion 12 of handle 10 abuts the rear surface of base 20. The rearwardly projecting pinion section 32 is disposed within slot 13 with the pinion teeth engaged by the teeth of rack 14. Slot 13 and rack 14 are considerably longer than the diameter of pinion section 32 to thereby permit longitudinal movement of distal handle portion 12 relative to rotary brush 30, whereby the rack can rotatably drive the pinion. Typically, the outside diameter of pinion section 32 is approximately sixty percent of the length of rack 14. In the illustrated embodiment, rack 14 has eleven teeth and pinion section 32 has seventeen teeth.

A nub 34 projects a short distance rearwardly from the rear surface of pinion section 32. Nub 34 has an arcuate tip, preferably a section of a sphere, disposed symmetrically about the central longitudinal axis of rotatable brush 30. The nub typically projects to an axial length that is between three and five percent of the axial length of the overall brush section 30; the nub diameter is typically between four and eight times the nub axial length.

The front surface of tuft supporting section 31 has a plurality of holes 35 defined partway into its depth. In the illustrated embodiment, twelve holes 35 are provided, eight of which are disposed at the same radial distance from the rotation axis at equiangularly spaced positions near the periphery of the surface; four holes 35 are located radially inward of the first eight holes at a second radial distance from the rotation axis. Each hole 35 has the bottom of a tuft 36 of brush bristles secured therein by means of a suitable adhesive. Tufts 36 are thus fixedly positioned in their respective holes 35 to extend perpendicularly from the front surface of brush section 30 and to rotate with that brush section about the rotation axis. In the preferred embodiment, bristles 36 of rotatable brush section 30 are shorter than the fixed bristles 26 projecting from base 20. In addition, bristles 36 are disposed between the two longitudinally spaced clusters of fixed bristles 26.

Cover 40 comprises a rear wall 41 and two side walls 42 and 43 extending forwardly from opposite longitudinal edges of rear wall 41. The spacing between side walls 42 and 43 corresponds substantially to the width of base 20 and the distal portion 12 of the handle so that both base 20 and portion 12 can be retained between the side walls. The forward and rearward ends of side walls 42 and 43 are bent inwardly at substantially the same angle as the chamfered corners of portion 12 and base 20 to prevent the base 20 and portion 12 from moving longitudinally out of the open longitudinal ends of the cover. In this regard, the length of cover 40 is chosen to permit base 20 to reside in the cover with all of its chamfered corners substantially abutting the inner surfaces of the bent ends of side walls 42, 43.

The inner surface of side walls 42, 43 have respective longitudinally extending recesses 44, 45 of generally rectangular configuration. Recesses 44, 45 extend throughout most of the length of the side walls and are spaced from rear wall 41. The configuration of recesses 44, 45 is selected to permit the recesses to receive respective lateral projections 24, 23 of base 20, whereby the base can be retained in cover 40 between side walls 42, 43 in snap-fit engagement. In this manner base 20 is prevented from moving in a forward or rearward direction out of cover 40. Since the bent ends of side walls 42, 43 retain the ends of the base against longitudinal movement relative to the cover, the base is securely held in the cover.

Centrally located on the interior surface of rear wall 41 is a dimpled bearing recess 46. The configuration of recess 46 is such that it receives projection 34 from rotatable brush section 30 and facilitates rotation of the projection therein about the brush rotation axis.

In assembling the brush, the forward portion 12 of handle 10 is first placed in cover 40 with the rear surface of portion 12 abutting the inner surface of rear wall 41 of cover 40. The width of handle portion 20 is selected such that its longitudinal sides slidably abut respective cover side walls 42, 43 at a location rearward of recesses 44, 45, the latter being fully exposed forwardly of portion 12. The fact that handle portion 12 is shorter than cover 40 permits considerable slack in longitudinally positioning portion 12 within the cover. However, for any longitudinal position of handle portion 12 within cover 40, bearing recess 46 is exposed through slot 13 and spaced from the slot ends by at least the radius of pinion 32. This permits rotatable brush 30 to be placed in cover 40 with projecting nub 34 disposed in bearing recess 46. In this position of rotatable brush 30, teeth of the pinion section 32 engage teeth of rack 14. The rear surface of intermediate ledge 33, having a diameter larger than the width of slot 13, abuts the forward surface of handle portion 12. Base 20 is then secured in cover 40 by first positioning the base such that tuft supporting section 31 of rotatable brush 30 extends into hole 21 (with tufts 36 projecting forwardly of the base if the tufts have previously been secured in holes 35). Lateral projections 23, 24 are then snapped into respective recesses 45, 44, taking advantage of the resilient flexibility of side walls 43, 42. When thusly assembled, as best illustrated in FIG. 2, the rear surfaces of base 20 and ledge 33 slidably abut the forward surface of handle portion 12 in flush relation. Ledge 33 is retained between base 20 and handle portion 12 to prevent axial movement of rotatable brush 30 while permitting the rotatable brush to rotate about its central longitudinal axis when driven by rack 14.

In operation, the head of the toothbrush is inserted into a person's mouth with the exposed tips of the bristles of fixed tufts 26 urged forwardly against the person's teeth. Assuming handle portion 12 to be initially fully extended into the brush head, as illustrated in FIG. 3, the handle may then be pulled in a direction away from the head while the bristles of fixed tufts 26 are urged forwardly against the teeth. As a result, fixed bristles 26 flex slightly away from the handle permitting the shorter rotatable bristle tufts 36 to contact the tooth surfaces. Frictional engagement of the bristles of fixed tufts 26 against the tooth surfaces minimizes movement of the brush head in response to the pulling force applied to the handle; instead, handle portion 12 slides rearwardly within cover 40 to cause rack 14 to rotatable drive pinion 32. Tufts 36 are thereby caused to rotate about the central longitudinal axis of brush section 30 to provide an arcuate sweeping motion across the surfaces of contacted teeth. After handle portion 12 reaches the proximal end of cover 40, continued pulling force applied to handle 10 causes the brush head to be pulled along with the handle without rotation of brush 30 and its bristle tufts 36. Instead, all of the bristle tufts 36 and 26 are pulled across the teeth to effect a transverse sweeping stroke. When handle 10 is pushed in the opposite direction, the bristles of fixed tufts 26 flex in the opposite direction and frictionally engage the teeth to positionally stabilize the head and permit handle portion 12 to move toward the distal end of the head. The distally directed movement of the handle portion 12 permits rack 14 to rotate pinion 32 and brush section 30 in the opposite direction, whereby the bristles in tufts 36 likewise rotate in the opposite direction about the axis of brush 30. When the distal end of handle portion 12 reaches the distal end of cover 40, rotation of brush 30 and its bristle tufts 36 terminates, and continued pushing movement of the brush handle causes the head and all of the bristles to be pushed accordingly. Continued longitudinal reciprocation of the handle results in oscillatory rotation of the rotatable tufts 36 in the same manner.

If the person using the brush decides to apply the rotary brush action to a particular tooth, he or she would intentionally limit the length of the reciprocating longitudinal handle strokes to only that distance necessary to effect rotation of pinion 32. Typically, this involves back and forth longitudinal strokes of approximately one-half inch in length. The point during each stroke at which rotation of pinion 32 terminates is readily sensed or felt by the person using the brush since the distal end of handle portion 12 impacts against the distal end of cover 40, or the proximal end of portion 12 impacts the proximal end of cover 40, depending upon the direction of handle movement. The brush head can be moved from tooth to tooth, on either exterior and interior tooth surfaces, to apply oscillatory rotatable brush action to all of the teeth in the person's mouth. If transverse linear brush strokes are desired, longer longitudinal strokes may be employed; if up and down strokes are desired, the brush is merely rotated about the handle axis in a conventional manner. The user of the brush may also rotate the brush handle about its longitudinal axis during rotary brushing to place desired groups of tufts in contact with the teeth as the handle is reciprocated.

The lengths of the bristles in fixed tufts 26 need not all be equal. It is particularly advantageous, for example, for the fixed bristles closest to the longitudinal center of the head to be shorter than the fixed bristles closest to the side walls of cover 40. Such an arrangement makes it easier for the fixed bristles to conform to teeth adjacent the tooth being rotatably brushed, particularly the incisors located at the curvatures in the jaw bone. Typically, the variation in fixed bristle lengths is a gradual taper from the innermost to the outermost bristles, and the maximum length difference is on the order of twenty percent. However, even the shortest fixed bristles are preferably longer than the rotatable bristles, thereby assuring that the fixed bristles frictionally engage tooth surfaces to prevent the brush head from moving longitudinally with the handle and thereby permitting rack 14 to rotatably drive pinion section 32.

A commercially important feature of the embodiment of FIGS. 1-5 is the use of only four parts that are easily and inexpensively assembled. These parts, namely handle 10, base 20, rotatable brush section 30 and cover 40, are each one-piece molded plastic units. Tufts 26, 36 may be secured in respective holes 25, 35 before or after the four parts are assembled.

The toothbrush of the present invention may be provided with a plurality of rotatable brush sections rather than the single rotatable brush section employed in the embodiment described in relation to FIGS. 1-5. A toothbrush having such plural rotatable brushes is illustrated in FIGS. 6-11 to which specific reference is now made. The modified toothbrushes includes the following assembled parts, namely: a handle 50; a base 60; ten rotatable brush members 70; and a cover 80. Base 60, rotatable brush members 70 and cover 80 comprise the toothbrush head. Handle 50 has a conventional proximal end and a shaft 51 and is provided with a flat apertured distal end portion 52. Two apertures in distal portion 52 take the form of parallel, longitudinally coextensive and generally rectangular slots 53a and 53b defined entirely through the thickness dimension of distal portion 52. Slots 53a and 53b are transversely spaced and each is enclosed on all four sides, their longer sides extending in the length dimension of the handle. The innermost longer sides of slots 53a and 53b have respective rows of regularly spaced tooth-like projections extending along substantially their entire length to define respective toothed longitudinal racks 54a and 54b facing inwardly of their respective slots. Distal portion 52 is somewhat wider than the rest of handle 50 and is provided with four chamfered exterior corners 55. The angle of the chamfered corners 55 is typically between fifty and sixty-five degrees to the longitudinal dimension of the brush, and the edges of the chamfer cuts may be rounded, if desired. The length of coextensive slots 53a and 53b is typically between seventy-five and ninety percent of the length of distal handle portion 52, and the length of racks 54a and 54b is typically between sixty and eighty percent of the slot length. Slots 53a and 53b are symmetrically disposed on opposite sides of the longitudinal centerline of distal handle portion 52.

Distal handle portion 52 has a pair of longitudinally extending alignment channels 56 and 57 defined in its front and rear surfaces, respectively. Channels 56 and 57 are substantially identical and are disposed transversely in between slots 53a and 53b so as to be parallel to the slots but not necessarily as long as the slots.

Base 60 is a generally rectangular plate having width and depth dimensions substantially the same as those of distal portion 52 of handle 50. The length of base 60, however, is significantly greater than the length of distal portion 52. Typically, the length of distal handle portion 52 is between fifty and seventy percent of the length of base 60. The outside corners of base 60 are chamfered at the same angle as the chamfered corners 55 of distal portion 52. A plurality of cylindrical holes are defined entirely through the thickness of base 60 at a plurality of spaced locations. In the embodiment illustrated in FIGS. 6-11, ten holes 61 are provided in two groups of five, each group of five comprising a longitudinally extending row disposed adjacent a respective longitudinal side of base 60. Throughout most of their axial lengths holes 61 have a first diameter. A very short segment of each hole 61, terminating at the rear surface of base 60, has a slightly larger diameter. The transition between the short segment and the rest of hole 61 is an annular shoulder facing toward the rear of base 60.

A pair of lateral projections 63, 64 extend along opposite longitudinal sides of base 60. Each projection 63, 64 extends transversely outward from its respective base side at a location intermediate the front and rear surfaces of the base. More particularly, each projection includes a forwardly facing surface or ledge extending perpendicularly from the base side wall, the surface having a transverse dimension typically on the order of approximately five percent of the width dimension of base 60. From this surface projections 63, 64 taper inwardly and rearwardly to intersect the rear surface of the base. The length of projections 63, 64 along their respective base sides is typically between sixty and eighty percent of the length of base 60.

The rear surface of base 60 includes an elongated projection 67 configured to be received and longitudinally slidable within channel 56 on the front surface of distal handle portion 52. Otherwise, the rear base surface is generally flat and is interrupted only by the diametrically widened rear segments of holes 61. The front surface of base 60 has multiple holes 65 defined partway into the base depth. Holes 65 are disposed between the two rows of holes 61 as well as at locations both proximally and distally beyond those rows. Each hole 65 has the bottom of a tuft of brush bristles secured therein by a suitable adhesive. Tufts 66 are thus fixedly positioned in their respective holes 65 to extend perpendicularly from the front surface of base 60. Typically, there are between forty and sixty stationary tufts 66 secured in respective holes 65 in the front surface of base 60.

Each rotatable brush 70 includes a forward tuft-supporting section 71, a rear pinion section 72 and an intermediate annular ledge 73 disposed axially between sections 71 and 72. Tuft-supporting section 71 may be a cylinder or right polyhedron having a diameter slightly smaller than the diameter of hole 61 in base 60. The axial length of section 71 corresponds substantially to the axial length of the portion of hole 61 disposed between the front surface of base 60 and the short diametrically enlarged segment of hole 61. Annular ledge 73 projects radially outward to a diameter slightly smaller than the diameter of the short segment of hole 61, and has an axial length substantially corresponding to the axial length of that short hole segment. The dimensions of section 71 and ledge 73 are such to permit the rotatable brushes 70 to rotate in respective holes 71 about the central longitudinal axes of the hole and brush. In this regard, each brush 70 is placed in base 60 by inserting section 71 into hole 61 from the rear of the base until ledge 73 abuts the annular shoulder between the short hole segment and the rest of hole 71. Thusly placed, the front surface of section 71 is substantially flush with the front surface of base 60, and the rear surface of annular ledge 73 is substantially flush with the rear surface of base 60. In this position of the rotatable brushes 70, their pinion sections 72 project rearwardly from base 60.

Each pinion section 72 is coaxial with its section 71 and its ledge 73 and has its radially extending teeth configured t mesh with the teeth in one of racks 54a or 54b in cooperative relation. Specifically, when the toothbrush is assembled, the front surface of distal handle portion 52 abuts the rear surface of base 60. The rearwardly projecting pinion section 72 of five of the brushes 70 are disposed in slot 53a with their pinion teeth engaged by the teeth of rack 54a. The pinion sections 72 of the other five brushes are disposed in slot 53b with their pinion teeth engaged by the teeth of rack 54b. Slots 53a and 53b and racks 54a and 54b are considerably longer than the rows of rotatable brushes 70 in order to permit considerable longitudinal movement of distal handle portion 52 relative to the rotary brushes 70, whereby the racks 54a and 54b can rotatably drive all of the pinion sections 72.

The rear surface of pinion sections 72 may be provided with bearing nubs similar to nub 34 (FIGS. 2, 3) that cooperate with respective bearing recesses or dimples in cover 80 in the manner described above in relation to the embodiment of FIGS. 1-5.

The front surface of each tuft-supporting section 71 has a plurality of holes similar to holes 35 in brush 30. Each such hole has the bottom of a tuft 76 of brush bristles secured therein by a suitable adhesive. Tufts 76 are thus fixedly positioned in their respective holes to extend perpendicularly from the front surface of brush sections 70 and to rotate therewith about the respective rotation axes of the brushes. In the preferred embodiment bristles 76 of rotatable brush sections 70 are shorter than the fixed bristles 66 projecting from base 60.

Cover 80 comprises a rear wall 81 and two side walls 82 and 83 extending forwardly from opposite longitudinal edges of rear wall 81. The spacing between side walls 82 and 83 correspond substantially to the width of base 60 and forward handle portion 52 so that both the base and the distal handle portion can be retained between the cover side walls. The forward and rearward ends of side walls 82 and 83 are bent inwardly at substantially the same angle as the chamfered corners of distal handle portion 52 and base 60 to prevent the base 60 and handle portion 52 from moving longitudinally out through the open longitudinal ends of the cover. In this respect, the length of cover 80 is chosen to permit base 60 to reside in the cover with all four of its chamfered corners substantially abutting the inner surfaces of the bent ends of side walls 82, 83.

The inner surface of side walls 82, 83 have respective longitudinally extending recesses 84, 85 of generally rectangular configuration. Recesses 84, 85 extend throughout most of the length of the side walls and are spaced from the rear wall 81. The configuration of recesses 84, 85 is selected to permit each recess to receive a respective lateral projection 64, 63, whereby base 60 can be retained in cover 80 between side walls 82, 83 in snap-fit engagement. Base 60 may thus be prevented from moving in a forward or rearward direction out of cover 80. Since the bent ends of side walls 82, 83 retain the ends of base 60 against longitudinal movement relative to cover 80, the base is securely held in the cover.

An elongated projection 87 extends in depth forwardly from rear wall 81. Projection 87 is configured to be slidably received in channel 57 at the rear surface of distal handle portion 52. Projections 87 and 67 are shorter in length than channels 56 and 57 in order to accommodate longitudinal displacement of handle portion 52 relative to base 60 and cover 80. The engagement of projection 67 in channel 56, and the engagement of projection 87 in channel 57, assure that the handle does not rotate (e.g., about a yaw axis) as the handle reciprocates. Accordingly, racks 54a and 54b remain properly aligned with the teeth in the pinion sections 72 as the handle reciprocates longitudinally.

In assembling the brush, the distal portion 52 of handle 50 is first placed in cover 80 with the rear surface of portion 52 abutting the inner surface of rear wall 81 of the cover, and with projection 87 received in channel 57 of handle portion 52. The width of handle portion 52 is such that its longitudinal sides slidably abut respective cover side walls 82, 83 at a location rearwardly of recesses 84, 85, the latter being fully exposed forwardly of distal handle portion 52. The fact that distal handle portion 52 is shorter than cover 80 permits considerable slack in longitudinally positioning the handle portion in the cover. However, for any longitudinal position of handle portion 52 in cover 80, projection 87 is disposed in channel 57. Rotatable brushes 70 are placed in respective holes 61 of base 60 which is then secured within cover 80 by first positioning the base such that tuft-supporting sections 71 of rotatable brushes 70 extend into holes 61 with tufts 76 projecting forwardly of the base. Lateral projections 63, 64 of the base are then snapped into respective recesses 85, 84, taking advantage of the resilient flexibility of side walls 83, 82. When thusly assembled, the rear surfaces of base 60 and ledges 73 slidably abut the forward surface of handle portion 52 in flush relation. Ledges 73 are retained between base 60 and handle portion 52 to prevent axial movement of rotatable brushes 70 while permitting the rotatable brushes to rotate about their central axes when driven by racks 54a and 54b.

Operation of the embodiment of FIGS. 6–11 is essentially similar to that described above for the embodiment of FIGS. 1–5. The fixed bristle tufts 66 serve to positionally stabilize the brush head by frictionally engaging the tooth surfaces so that all ten rotatable brushes 70 may be cyclically rotated by longitudinal reciprocation of handle 50. The placement of plural rotatable brushes 70 in a longitudinal row permits plural adjacent teeth to be rotatedly brushed simultaneously without repositioning the brush head. The use of two rows of rotatable brushes permits upper and lower teeth to be simultaneously brushed with rotating strokes.

Figure 12:
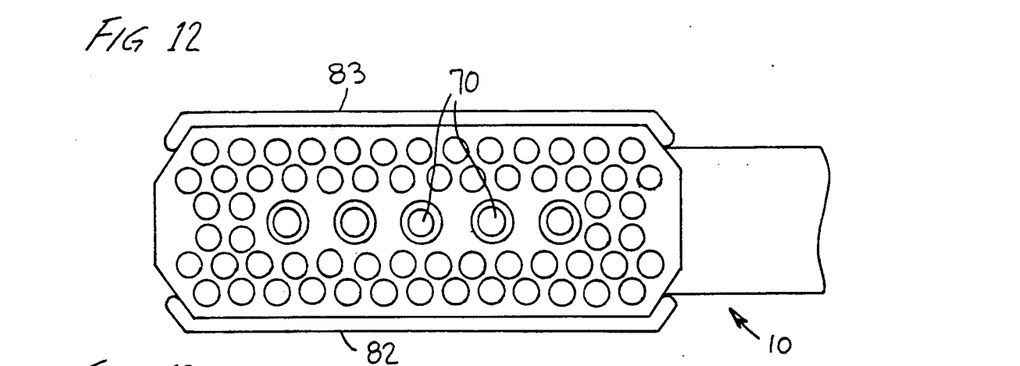
FIG. 12 is a top view in plan of a third toothbrush embodiment constructed in accordance with the principles of the present invention.
Figure 13:
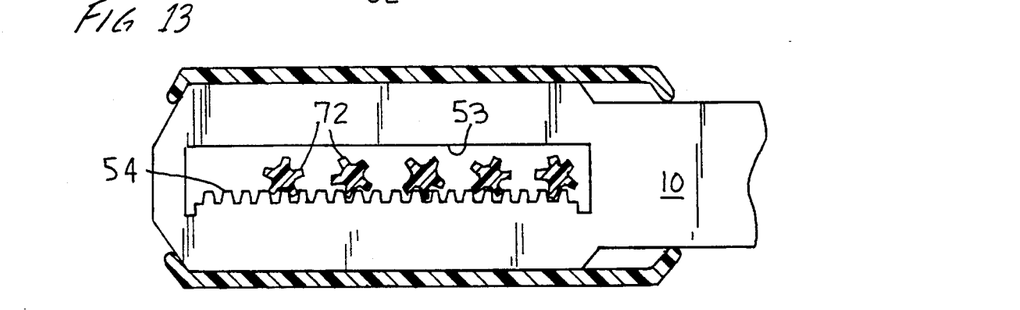
FIG. 13 is a view in longitudinal section, similar to FIG. 10 but of the toothbrush illustrated in FIG. 12.
Figure 14:
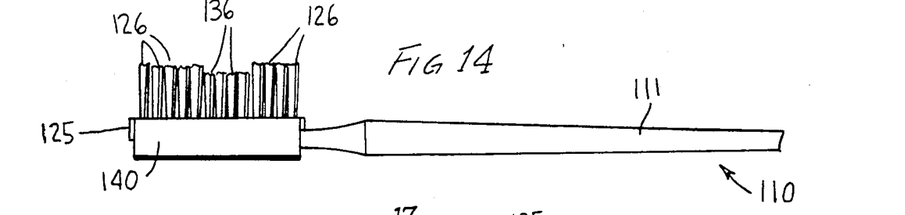
FIG. 14 is a side view in elevation of a fourth toothbrush embodiment constructed in accordance with the principles of the present invention.
Figures 15, 16, 17:
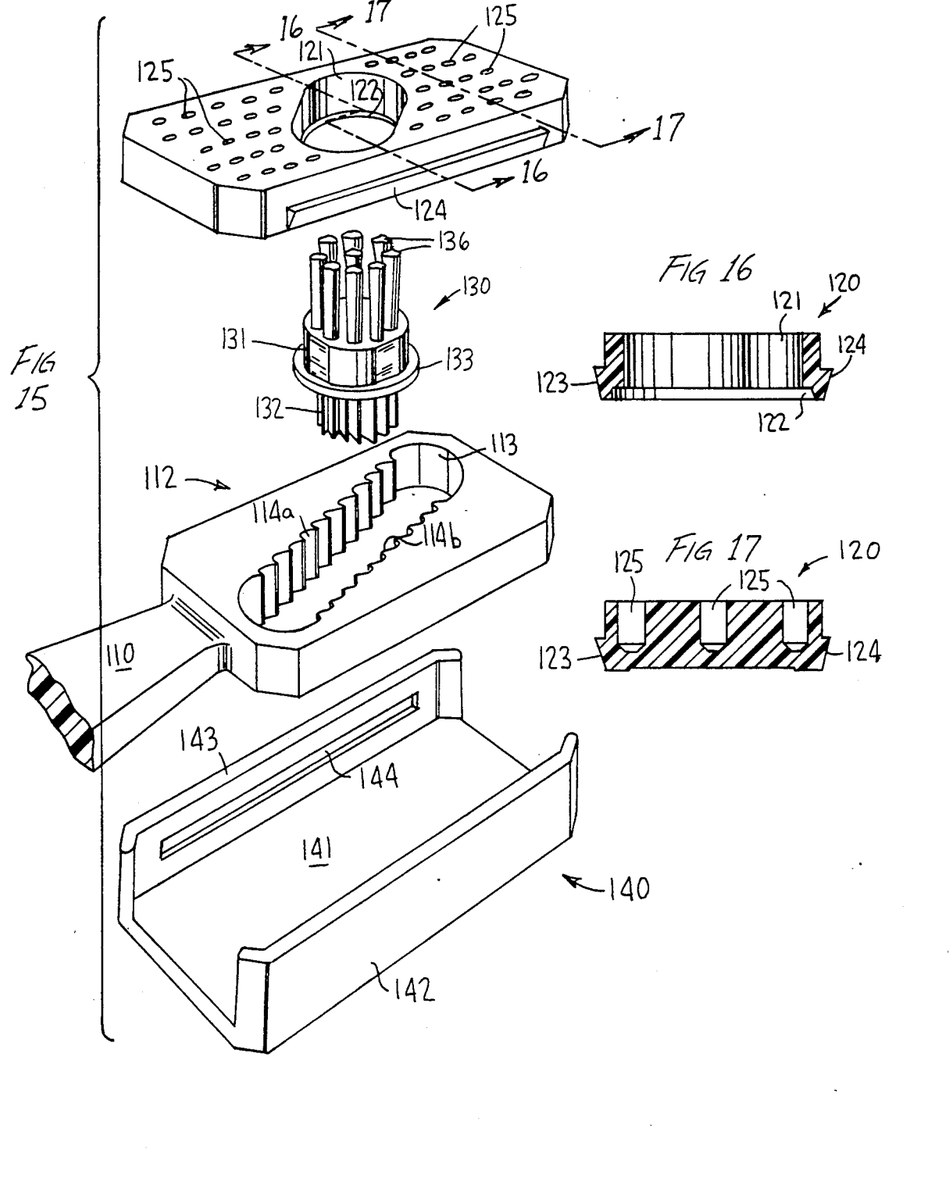
FIG. 15 is an exploded view in perspective of the toothbrush illustrated in FIG. 14.
FIG. 16 is a view in section taken along lines 16—16 of FIG. 15.
FIG. 17 is a view in section taken along lines 17—17 of FIG. 15.

The positioning of plural rotatable brushes on the brush head can be varied as desired. One alternative practical example of this is illustrated in FIGS. 12 and 13 wherein a single row of five rotatable brushes 70 is shown extending along the longitudinal center of the brush head. Fixed tufts 66 are disposed on opposite sides of the row as well as proximally and distally of the row. Only a single rack 54 and single slot 53 are required to drive the single row of pinion sections 72.

The embodiments described thus far operate in a manner whereby one or more rotatable brushes is caused to cyclically rotate in opposite directions in response to longitudinal reciprocation of the brush handle. In accordance with one aspect of the present invention, one or more rotatable brush sections is caused to rotate in only one direction irrespective of the longitudinal direction of the reciprocating handle. An embodiment possessing this feature is illustrated in FIGS. 14–19 to which specific reference is now made. This embodiment includes four assembled parts, namely: a handle 110; a base 120; a rotatable brush member 130; and a cover 140. Base 120, rotatable brush member 130 and cover 140 comprise the toothbrush head. Handle 110 is similar in most respects to handle 10 (FIGS. 1–5) and includes a shaft 111 and a flat apertured distal end portion 112. However, the aperture in distal handle portion 112 takes the form of a generally rectangular slot 113 having semi-circular ends. Slot 113 is enclosed on all four sides and has its longer sides extending at an acute angle, typically ten degrees, to the length dimension of the handle. Each of the longer sides of slot 113 has a respective row of regularly spaced tooth-like projections extending along substantially its entire length to define respective toothed longitudinal racks 114a and 114b facing each other and inwardly of slot 113. Distal portion 112 is somewhat wider than the rest of handle 110 and is provided with four chamfered exterior corners in the manner described above. The length of slot 113 is typically between seventy-five to ninety percent of the length of distal handle portion 112, and the length of racks 114a and 114b is between sixty and eighty percent of the slot length. The width of slot 113 is typically between forty and seventy-five percent of the width of distal portion 112. The individual teeth of racks 114a and 114b are preferably sawtooth shaped as compared to the symmetrical teeth employed in previously described embodiments. The teeth of rack 114a slope toward the distal end of the handle, whereas the teeth of rack 114b slope toward the proximal end of the handle.

Base 120 is a generally rectangular plate member similar in all respects to base 20 (FIGS. 1–5) except that its central hole 121 takes the form of a slot having straight sides and semicircular ends. Slot 121 is considerably shorter than slot 113 in distal handle portion 112 and is oriented at a greater acute angle to the longitudinal dimension of the handle than is slot 113. The length of slot 121 is typically approximately two-thirds of the length of slot 113 and forms an angle of approximately forty degrees with the longitudinal dimension of the toothbrush. Slot 121 is defined entirely through the thickness of base 120 at a location substantially central of both the length and width dimensions. Throughout most of its depth dimension slot 121 is uniformly dimensioned in length and width in that its length and width remain constant at different depths. However, a very short segment 122 of slot 121, terminating at the rear surface of base 120, has slightly larger length and width dimensions. The transition between segment 122 and the rest of slot 121 is a shoulder bordering slot 121 and facing toward the rear of base 120.

A pair of lateral projections 123, 124 extend along opposite longitudinal sides of base 120. Each projection 123, 124 extends outwardly from its respective base side at a location intermediate the front and rear surfaces of the base. More particularly, each projection includes a forwardly facing surface or ledge extending perpendicularly from the base side wall, the surface having a transverse dimension typically on the order of approximately five percent of the width dimension of base 120. From this surface projections 123 and 124 taper inwardly and rearwardly to intersect the rear surface of the base. The length of projections 123, 124 along their respective base sides is typically between sixty and eighty percent of the length of base 120.

The rear surface of base 120 is generally flat and is interrupted only by the widened segment 122 of slot 121. The front surface of the base has multiple holes 125 defined partway into the base depth. Holes 125 are disposed in two clusters, one cluster positioned forwardly of slot 121, the other positioned rearwardly of that slot. Each hole 125 has the bottom of a tuft 126 of brush bristles secured therein by a suitable adhesive. Tufts 126 are thus fixedly positioned in their respective holes 125 to extend perpendicularly from the front surface of base 120. Typically, there are between forty and sixty stationary tufts secured in respective holes 125 in the front surface of base 120.

Rotatable brush 130 includes a forward tuft-supporting section 131, a rear pinion section 132 and an intermediate annular ledge 133 disposed axially between sections 131 and 132. Tuft-supporting section 131 may be a cylinder or right polyhedron having a diameter smaller than the width of slot 121 in base 120. The axial length of section 131 corresponds substantially to the axial length of the portion of slot 121 disposed between the front surface of base 120 and slot segment 122. Annular ledge 133 projects radially outward to a diameter slightly smaller than the width of slot segment 122 but larger than the width of slot 121, and has an axial length substantially corresponding to the depth of slot segment 122. The dimensions of section 131 and ledge 133 are such to permit the rotatable brush 130 to rotate in and move along the length of slot 121, the rotation being about the central longitudinal axis of the brush 130. In this regard, brush 130 is placed in base 120 by inserting section 131 into slot 121 from the rear of the base until ledge 133 abuts the annular shoulder between slot segment 122 and the rest of slot 121. Thusly placed, the front surface of section 131 is substantially flush with the front surface of base 120, and the rear surface of annular ledge 133 is substantially flush with the rear surface of base 120. In this position of the rotatable brush 130, pinion section 132 projects rearwardly from base 120. Importantly, the diameters of section 131 and ledge 133 are sufficiently smaller than the width of slot 121 and slot segment 122, respectively, to provide positional slack for brush 130 transversely in slot 121. This positional slack is selected to permit the teeth of pinion section 132 to contact the teeth of only one of racks 114a and 114b at any one time. In this regard, pinion section 132 is coaxial with section 131 and ledge 133 and has its radially extending teeth configured to mesh with the teeth of either rack 114a or 114b in cooperative relation. Specifically, when the toothbrush is assembled, the front surface of distal portion 112 of handle 110 abuts the rear surface of base 120; the rearwardly projecting pinion section 132 is disposed within slot 113. When the handle 110 is pushed in a distal direction, angled rack 114a is pushed against the pinion section 132 and engages its teeth to rotate brush 130. When the handle is pulled in a proximal direction, angled rack 114a disengages from the pinion 132 while angled rack 114b engages the pinion and rotates the brush 130. Racks 114a and 114b are considerably longer than the diameter of pinion section 132 to thereby permit longitudinal movement of distal handle portion 112 relative to brush 130, whereby the racks can rotatably drive the piston.

The front surface of tuft-supporting section 131 has a plurality of holes defined pathway into its depth. In the illustrated embodiment, nine such holes are provided, eight of which are disposed at the same radial distance from the rotation axis at equiangular spaced positions near the periphery of the surface; one hole is located on the rotation axis. Each of these holes has the bottom of a tuft 136 of brush bristles secured therein by means of a suitable adhesive. Tufts 136 are thus fixedly positioned in their respective holes to extend perpendicularly from the front surface of brush section 130 and to rotate with that brush section about the rotation axis. In the preferred embodiment, bristles 136 of rotatable brush section 130 are shorter than the fixed bristles 126 projecting from base 120. In addition, bristles 136 are disposed between the two longitudinally spaced clusters of fixed bristles 126.

Cover 140 is substantially identical to cover 40 (FIGS. 1-5) and comprises a rear wall 141, two side walls 142 and 143 and longitudinally extending recesses 145, 144 in respective side walls. The details of the cover are described above in relation to FIGS. 1-5. There is no dimpled bearing provided in rear wall 141 in view of the fact that rotatable brush 130 does not remain positionally fixed relative to that wall. In addition, assembly of the brush components is effected in the manner described above in relation to FIGS. 1-5.

Figures 18, 19, 20A:
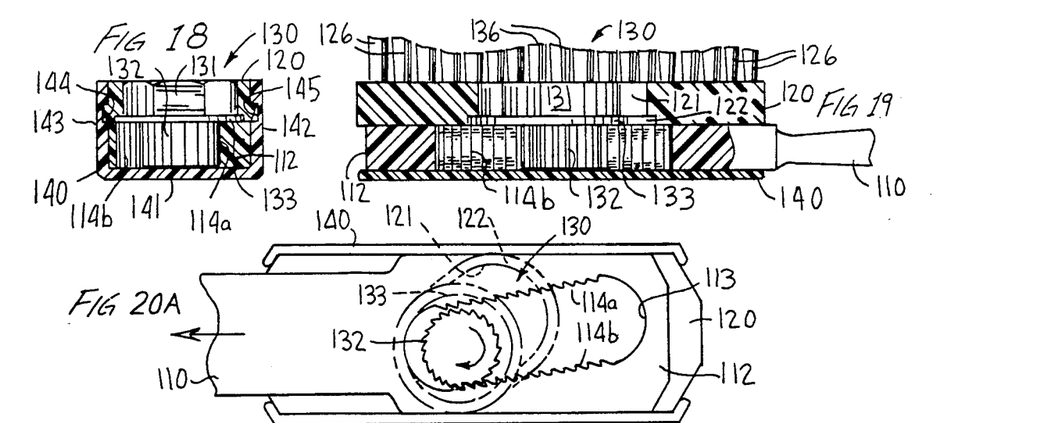
FIG. 18 is a view in transverse section of the toothbrush illustrated in FIG. 14.
FIG. 19 is a view in longitudinal section of the toothbrush illustrated in FIG. 15.
FIGS. 20A through 20E are diagrammatic illustrations of different respective positions of a rotatable brush section of the toothbrush illustrated in FIG. 15.

Operation of the toothbrush is diagrammatically represented in FIGS. 20A through 20E. Referring to FIG. 20A, rotatable brush 130 is positioned at the proximal end of slot 113 and the proximal end of slot 122. Handle portion 112 is at its distalmost position within cover 140 and, as indicated by the linear arrow, is just beginning to be pulled in a proximal direction. The proximally directed longitudinal force urges the angled rack 114b into engagement with the teeth of pinion 132 and disengages the similarly angled rack 114a from the pinion.

Figure 20B:
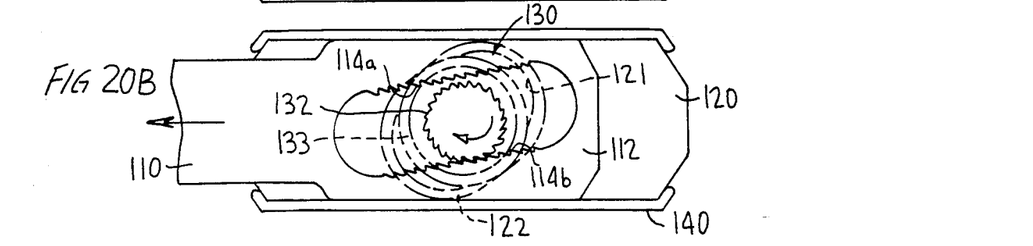

In FIG. 20B distal handle portion 112 is shown having been pulled approximately halfway through its proximally directed stroke. Rotatable brush 130 is disposed at approximately the longitudinal centers of both slots 113 and 122. Rack 114b fully engages pinion 132 during this stroke and rotates the pinion clockwise as represented by the arcuate arrow.

Figure 20C:
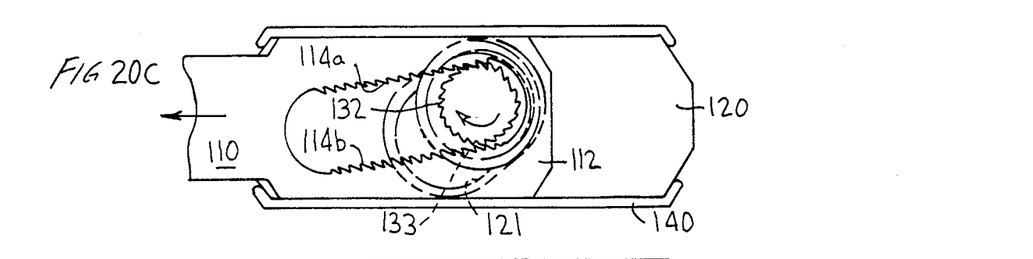

In FIG. 20C handle portion 112 is approaching the end of its proximally directed stroke, and brush 130 is approaching the distal end of slot 113 while rack 114b is still pulled into engagement with pinion 132. Brush 130 continues its clockwise rotation.

Figure 20D:
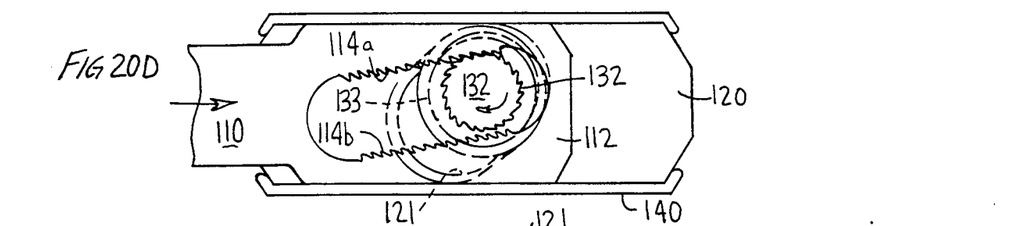

FIG. 20D illustrates the unit shortly after handle 110 has begun its distally directed pushing stroke. Rack 114b has been pushed away from its engagement with pinion 132 while rack 114a has been pushed into engagement with the pinion. Importantly, the rotatable driving force exerted by rack 114a on pinion 132 is in the same direction (i.e., clockwise) as the rotational driving force previously exerted by rack 114b. This results from the fact that the racks are located on diametrically opposite sides of the pinion and move in opposite longitudinal directions when engaging the pinion. The diametric slack between pinion 132 and the opposing racks 114a, 114b permits only rack 114a to engage the pinion when the handle is pushed distally and only rack to 114b engage the pinion when the handle is pulled proximally.

Figure 20E:
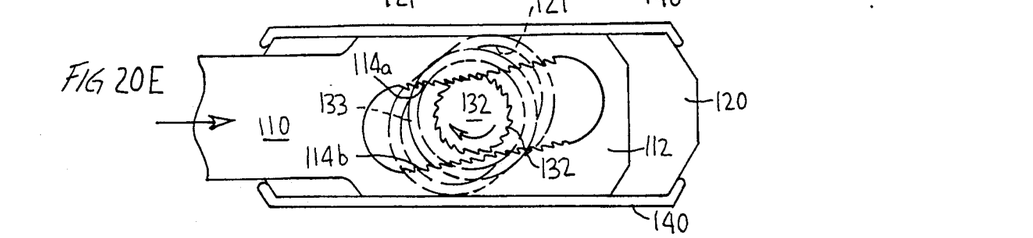

In FIG. 20E the distally directed handle stroke is shown further along its path, and brush 130 is located intermediate the ends of slot 113. Rack 114a remains pushed into engagement with pinion 132 and continues to rotate the pinion clockwise.

From the foregoing description and from FIGS. 20A through 20E it will be understood that continued longitudinal reciprocation of handle 110 causes brush 130 to rotate in only one direction (i.e., clockwise) as it is alternately driven by racks 114a and 114b moving in opposite longitudinal directions.

Placement of slot 113 at an acute angle to longitudinal is what permits its sidewall racks 114a and 114b to be selectively and individually moved toward engagement with the pinion 132 as handle portion 112 moves longitudinally in different directions. The larger acute angle formed by the smaller slot 122 permits positive engagement between each rack and the pinion. Specifically, when the handle is pushed distally, rack 114a is pushed into the pinion and causes the rotary brush to be pushed against the opposite wall of slot 121. This firmly engages brush 130 between rack 114a and the wall of slot 121 to permit the rack to positively engage the pinion and rotate the brush. Likewise, when rack 114b is pulled into pinion 132, brush 130 is forced against the opposite side wall of slot 121 so that it may be positively rotated by rack 114b.

As in the previously described embodiments, it is the positional stabilization of the brush head by frictional engagement between the fixed bristles in tufts 126 and the tooth surfaces that permits brush 130 to be rotated in response to longitudinal handle reciprocation.

It will be appreciated that the present invention provides a method and apparatus for converting longitudinal reciprocation of the toothbrush handle into rotation of bristle tufts about axes oriented generally perpendicular to the longitudinal motion of the handle. The rotated bristles provide the desired rotary brushing action for removing built-up deposits on tooth surfaces. This desirable result is achieved without an electrical, mechanical or fluid pressure motor. Importantly, in order to keep the brush head from moving with the handle during longitudinal reciprocation of the handle, the head is provided with fixed bristle tufts or their equivalent in addition to the rotary bristles. The fixed bristles frictionally engage the tooth surface to positionally stabilize the brush head while the rotary bristles rotate in response to the longitudinal reciprocation of the handle within the brush head.

The particular mechanism disclosed herein for converting linear reciprocation of the handle to rotation of the rotatable brushes, namely a rack and pinion, is highly efficient and advantageous in the present context and constitutes the preferred mechanism for this function. However, it is important to note that other mechanisms for converting linear motion to rotary motion may be employed without departing from the scope of the invention. In this regard, it is the use of stationary bristles, or their equivalent, to positionally stabilize the brush head by frictionally engaging surfaces of teeth that is the seminal feature of the invention. This feature permits manual reciprocation of the handle relative to the brush head so that this relative motion can be converted to rotary brush motion.

In the embodiments illustrated and described above, each of the covers 40, 80 and 140, the bases 20, 60 and 120, the rotary brush members 30, 70 and 130, and the handles 10, 50 and 110 are one piece of molded plastic material. The pieces are easily assembled in the manner described without the need for adhesives, screws or pins, or the like except for the use of adhesive in securing the tufts of bristles to the bases and rotatable brush members It is to be understood that this type of advantageous construction is a subsidiary feature of the invention and not a limiting feature on the primary concept of utilizing stationary bristles or their equivalent to positionally stabilize the brush head to prevent linear motion of the handle relative to the stabilized head in order to effect rotation of the rotatable brushes.

All of the disclosed embodiments utilize positionally fixed bristles to frictionally engage tooth surfaces for the purpose of positionally stabilizing the tooth brush head. This arrangement is particularly advantageous since the fixed bristles can also effect longitudinal brushing when desired. However, it is to be understood that other elements or means may be used in place of the fixed bristles for stabilizing the brush head by frictionally engaging tooth surfaces. By way of example only, rubber or rubber-like plastic projections secured to the brush head may replace the fixed bristle tufts. In this regard, the important feature is the use of some means, fixed bristles or otherwise, secured to the brush head to positionally stabilize the brush head by engaging teeth s that the handle is capable of moving relative to the stabilized head and thereby rotatably drive the rotatable brushes.

It is preferred, but no means necessary for effective operation, that the bristles in the rotatable brush members not extend as far forward as the stationary bristles, thereby rendering the tips of the rotatable bristles recessed slightly relative to the tips of the stationary bristles. It is also preferred that the bristles on the rotatable brush members be softer and more flexible than the stationary bristles. Both of these features aid in the rotary cleaning action. Specifically, recessing the rotatable bristle tips relative to the stationary bristle tips requires that the stationary bristles be bent (i.e., in the direction opposite to handle movement) before the rotating bristle tips contact the user's teeth. This causes a portion of the stationary bristle length, not merely the tips, to contact the tooth surfaces and thereby introduce greater frictional engagement to resist brush head movement along with the handle. The softer rotary bristles permit these bristles to sweep across the tooth surfaces more efficiently. In other words, the harder and more rigid stationary bristles tend to remain stationary and in frictional engagement with the tooth surfaces while the softer more flexible bristles are rotatably swept across the tooth surfaces. These two features (i.e., the recessed rotatable bristle tips and the softer rotatable bristles) may be used together, or individually, or not at all, depending on the desired operation for particular embodiments.

In the embodiments described above, it is preferred that the rotatable brush members rotate approximately 360° in response to each complete linear stroke of the handle. This is a preference only and is not intended to be a limiting factor of the invention. It will be appreciated, of course, that the user of the toothbrush need not necessarily apply complete strokes but, instead, may reciprocate the handle without ever reaching the extreme distal and proximal positions of the distal handle portion within the brush head cover. Likewise, the user may push or pull the handle after the extreme positions are reached to cause the head to move longitudinally and effect linear strokes after the rotary stroke is completed. It is thus the user, and not a power driven mechanism, that controls the nature of the rotary/linear brush stroke that is applied to his or her own teeth.

Having described preferred embodiments of a new and improved method and apparatus for brushing teeth with rotating brush strokes according to the present invention, it is believed that other modifications, variations and changes will be suggested to those skilled in the art in view of the teachings set forth herein. Accordingly, it is to be understood that all such variations, modifications and changes are believed to fall within the scope of the present invention as defined by the appended claims.

What is claimed is:

1. A manually operated toothbrush comprising:
a handle elongated in a longitudinal dimension and adapted to be held by a human hand and manually reciprocated longitudinally;
a brush head having a first surface;
a plurality of positionally rotatable brush bristles extending away from said brush head in a direction generally perpendicular to said first surface;
means movably securing said handle to said brush head for permitting longitudinal movement of said handle relative to said brush head;
motion conversion means responsive to manually induced reciprocating linear motion of said handle along said longitudinal dimension relative to said brush head for rotating said plurality of rotatable brush bristles about an axis perpendicular to said first surface; and
position stabilization means secured to said brush head for engaging tooth surfaces to oppose longitudinal movement of said brush head along with said handle in response to longitudinal reciprocation of said handle.

2. The toothbrush according to claim 1 wherein said brush head is an assembly of three separate parts comprising:
a cover;
a base mounted in fixed position in said cover and including said first surface; and
a rotatable brush member rotatably mounted on said base and having said rotatable bristles secured thereto;
wherein said handle has a distal portion secured in said cover adjacent said base to permit longitudinal movement of said distal portion relative to said cover and said base; and
wherein said motion conversion means comprises a mechanical engagement between said distal portion of said handle and said rotatable brush member.

3. The toothbrush according to claim 2 wherein said mechanical engagement comprises a toothed rack on said distal handle portion and a toothed pinion on said rotatable brush.

4. The toothbrush according to claim 3 wherein said position stabilization means comprises a plurality of positionally fixed brush bristles secured to said base and arranged in two spaced clusters disposed on opposite longitudinal sides of said rotatable brush member.

5. The toothbrush according to claim 2 wherein said cover has a rear wall and two transversely spaced longitudinally extending side walls and is open at its longitudinal ends, wherein said base has a plate-like configuration and is secured to said side walls in snap-fit engagement in spaced relation from said rear wall, and wherein said distal handle portion is trapped in the space between said base and said rear wall so as to be restricted from all motion except linear longitudinal reciprocation relative to said base and cover.

6. The toothbrush according to claim 5 further comprising a plurality of rotatable brush members rotatably mounted on said base, each rotatable brush member having a plurality of said rotatable bristles secured thereto, wherein said motion conversion means comprises a mechanical engagement between said distal handle portion and each of said rotatable brush members.

7. The toothbrush according to claim 6 wherein each of said rotatable brush members includes a tuft-supporting section having a forward surface from which said rotatable bristles extend, and a pinion section projecting from said base into the space between said base and said rear wall; and
wherein said mechanical engagement comprises toothed rack means disposed on said distal handle portion for engaging the pinion section of each rotatable brush member to rotate each brush member in response to longitudinal motion of said handle.

8. The toothbrush according to claim 7 wherein said plural rotatable brush members are arranged in a longitudinally extending row, and wherein said toothed rack means comprises a linear rack extending longitudinally and in engagement with the pinion section of each rotatable brush member in said row.

9. The toothbrush according to claim 7 wherein said plural rotatable brush members are arranged in first and second longitudinally extending rows, and wherein said toothed rack means comprises first and second linear racks extending longitudinally and in engagement with the pinion section of each brush in said first and second rows, respectively.

10. The toothbrush according to claim 5 wherein said rotatable brush member includes a tuft-supporting section having a forward surface from which said rotatable bristles extend, and a pinion section projecting from said base into the space between said base and said rear wall; and
wherein said mechanical engagement includes toothed rack means disposed on said distal handle portion for engaging said pinion section to rotate said brush member in response to longitudinal motion of said handle.

11. The toothbrush according to claim 10 wherein said toothed rack means comprises a rack extending longitudinally along said distal handle portion to rotate said pinion section and said brush member in a first rotary direction in response to distally directed motion of said handle relative to the brush head, and to rotate said pinion section and said brush member in a second rotary direction opposite to said first rotary direction in response to proximally directed motion of said handle relative to said brush head.

12. The toothbrush according to claim 10 wherein said toothed rack means comprises first and second racks extending in spaced parallel relation along opposite diametric sides of said pinion section and at a small acute angle to the longitudinal dimension of said handle, said first and second racks being spaced sufficiently and positioned such that only said first rack operatively engages and rotates said pinion section during distally directed motion of said distal handle portion, and only said second rack operatively engages and rotates said pinion section during proximally directed motion of said handle portion, whereby both racks rotate the pinion section in the same rotation direction.

13. The toothbrush according to claim 1 wherein said position stabilization means comprises a plurality of positionally fixed brush bristles extending generally perpendicularly from said first surface and arranged in two spaced clusters disposed on opposite longitudinal sides of said plurality of positionally rotatable brush bristles.

14. The toothbrush according to claim 1 further comprising at least one rotatable brush member rotatably mounted on said brush head to be rotated by said motion conversion means in response to linear motion of said handle relative to said brush head, wherein said rotatable brush bristles are secured to said rotatable brush member.

15. The toothbrush according to claim 1 further comprising a plurality of rotatable brush members rotatably mounted on said brush head, each rotatable brush member having a plurality of said rotatable bristles secured thereto, wherein said motion conversion means comprises a mechanical engagement between said handle and each of said rotatable brush members.

16. The toothbrush according to claim 15 wherein each of said rotatable brush members includes a tuft-supporting section having a forward surface from which said rotatable bristles extend, and a pinion section projecting rearwardly of said tuft-supporting section; and
wherein said mechanical engagement includes toothed rack means disposed on said handle for engaging the pinion section of each rotatable brush member to rotate each rotatable brush member in response to longitudinal motion of said handle.

17. The toothbrush according to claim 16 wherein said plural rotatable brush members are arranged in a longitudinally extending row, and wherein said toothed rack means comprises a linear rack extending longitudinally and in engagement with the pinion section of each rotatable brush member in said row.

18. The toothbrush according to claim 16 wherein said plural rotatable brush members are arranged in first and second longitudinally extending rows, and wherein said toothed rack means comprises first and second linear racks extending longitudinally and in engagement with the pinion section of each brush in said first and second rows, respectively.

19. The toothbrush according to claim 1 further comprising a rotatable brush member rotatably mounted on said brush head and having said rotatable bristles secured thereto, wherein said rotatable brush member includes a tuft-supporting section having a forward surface from which said rotatable bristles extend, and a pinion section projecting rearwardly from said tuft-supporting section; and wherein said motion conversion means comprises toothed rack means for engaging said pinion section to rotate said rotatable brush member in response to longitudinal motion of said handle.

20. The toothbrush according to claim 19 wherein said toothed rack means comprises a rack extending longitudinally in said brush head rearwardly of said tuft-supporting section to rotate said pinion section and said brush member in a first rotary direction in response to distally directed motion of said handle relative to said brush head, and to rotate said pinion section and said brush member in a second rotary direction opposite to said first rotary direction in response to proximally directed motion of said handle relative to said brush head.

21. The toothbrush according to claim 19 wherein said toothed rack means comprises first and second racks extending in transversely spaced parallel relation along opposite diametric sides of said pinion section and at a small acute angle to the longitudinal dimension of said handle, said first and second racks being spaced sufficiently and positioned such that only said first rack operatively engages and rotates said pinion section during distally directed motion of said handle relative to said brush head, and only said second rack operatively engages and rotates said pinion section during proximally directed motion of said handle relative to said brush head, whereby both racks rotate the pinion section in the same rotation direction.

22. The toothbrush according to claim 1 wherein said motion conversion means comprises means for rotating said plurality of rotatable brush bristles in first and second opposite rotation directions in response to first and second linear motion directions, respectively, of said handle relative to said brush head.

23. The toothbrush according to claim 1 wherein said motion conversion means comprises means for rotating said plurality of rotatable brush bristles in a common rotation direction in response to first and second directions of linear motion of said handle relative to said brush head.

24. The toothbrush according to claim 1 wherein said position stabilization means comprises a plurality of positionally fixed brush bristles extending in a generally perpendicular direction from said first surface, and wherein said positionally fixed brush bristles extend in length further from said first surface than do said positionally rotatable bristles.

25. The toothbrush according to claim 24 wherein said plurality of positionally fixed brush bristles are arranged in two spaced clusters disposed on opposite longitudinal sides of said plurality of positionally rotatable brush bristles.

26. The toothbrush according to claim 24 wherein said positionally rotatable bristles are more flexible than said positionally fixed bristles.

27. The toothbrush according to claim 1 wherein said position stabilization means comprises a plurality of positionally fixed brush bristles extending in a generally perpendicular direction from said first surface, and wherein said positionally rotatable bristles are more flexible than said positionally fixed bristles.

28. The method of applying rotational brush strokes to teeth in response to hand-powered longitudinally reciprocating motion of a handle of a toothbrush, said method comprising the steps of:
(a) positionally stabilizing a brush head of said toothbrush relative to the handle by frictionally engaging tooth surfaces with a projection secured in fixed relation to the brush head in order to oppose longitudinal movement of said brush head due to longitudinal reciprocation of said handle;
(b) longitudinally sliding said handle back and forth within said brush head in response to longitudinal reciprocation of said handle when said projection is in frictional engagement with said tooth surfaces; and
(c) in response to said back and forth sliding of said handle within said brush head, rotating a plurality of rotatable brush bristles secured to said head about an axis oriented generally perpendicular to said longitudinal sliding motion.

29. The method according to claim 28 wherein step (c) includes rotating said plurality of rotatable brush bristles in first and second opposite rotational directions in response to said back and forth sliding, respectively, of said handle within said brush head.

30. The method according to claim 28 wherein step (c) includes rotating said plurality of rotatable brush bristles in only one rotational direction in response to both said back and forth sliding of said handle within said brush head.

31. The method according to claim 28 wherein step (a) comprises frictionally engaging said tooth surfaces with multiple brush bristles positionally fixed and secured to said brush head.

32. A brush comprising:
a handle having a distal portion;
a brush head having a first surface;
a first plurality of tufts of brush bristles fixedly mounted on said first surface;
a generally cylindrical rotatable brush member mounted on said brush head for rotation about an axis oriented generally parallel to said bristles in said first plurality of tufts;
a second plurality of tufts of brush bristles mounted on said rotatable brush member to extend generally parallel to said bristles in said first plurality of tufts;
means for slidably securing said distal handle portion to said brush head to permit longitudinal movement of said handle relative to said brush head; and
motion conversion means responsive to longitudinal movement of said distal handle portion within said brush head for rotating said rotatable brush member and said second plurality of tufts about said axis.

33. The brush according to claim 32 further comprising a third plurality of tufts of brush bristles fixedly mounted on said first surface in parallel relation to the bristles of said first and second pluralities of tufts, wherein said first and third pluralities of tufts are spaced from one another on opposite longitudinal sides of said rotatable brush member.

34. The brush according to claim 33 wherein said means for slidably securing said distal handle portion to said brush head includes an elongated recess in said brush head for receiving said distal handle portion in longitudinally slidable relation, and wherein said motion conversion means comprises:
 a toothed pinon secured to said rotatable brush member and disposed in said elongated recess for rotation therein, said pinion having a rotation axis corresponding to the rotation axis of said rotatable brush member; and
 a toothed rack secured to said distal portion of said handle in interacting relation with said pinion to rotate said pinion as said distal handle portion moves longitudinally within said elongated recess.

35. The brush according to claim 32 wherein said brush head includes:
 a cover;
 a base mounted in fixed position in said cover and including said first surface;
 wherein said rotatable brush member is rotatably mounted on said base;
 wherein said distal handle portion is disposed within said cover adjacent said base to permit longitudinal reciprocating movement of said distal handle portion relative to said base and said cover; and
 wherein said motion conversion means comprises a mechanical engagement between said distal handle portion and said rotatable brush member.

36. The brush according to claim 35 wherein said mechanical engagement comprises a toothed rack on said distal handle portion and a toothed pinion on said rotatable brush.

37. The brush according to claim 36 wherein said cover has a rear wall and two transversely spaced longitudinally extending side walls and is open at its longitudinal ends, wherein said base has a plate-like configuration and is secured to said side walls in snap-fit engagement in spaced relation from said rear wall, and wherein said distal handle portion is trapped in the space between said base and said rear wall so as to be restricted from all motion except linear longitudinal reciprocation relative to said base and cover.

38. The brush according to claim 37 further comprising a plurality of rotatable brush members rotatably mounted on said base, each rotatable brush member having a plurality of said rotatable bristles secured thereto, wherein said motion conversion means comprises a mechanical engagement between said distal handle portion and each of said rotatable brush members.

39. The brush according to claim 38 wherein each of said rotatable brush members includes a tuft-supporting section having a forward surface from which said rotatable bristles extend, and a pinion section projecting from said base into the space between said base and said rear wall; and
 wherein said mechanical engagement comprises toothed rack means disposed on said distal handle portion for engaging the pinion section of each rotatable brush member to rotate each brush member in response to longitudinal motion of said handle.

40. The brush according to claim 39 wherein said plural rotatable brush members are arranged in a longitudinally extending row, and wherein said toothed rack means comprises a linear rack extending longitudinally and in engagement with the pinion section of each rotatable brush member in said row.

41. The brush according to claim 39 wherein said plural rotatable brush members are arranged in first and second longitudinally extending rows, and wherein said toothed rack means comprises first and second linear racks extending longitudinally and in engagement with the pinion section of each brush in said first and second rows, respectively.

42. The brush according to claim 37 wherein said rotatable brush member includes a tuft-supporting section having a forward surface from which said rotatable bristles extend, and a pinion section projecting from said base into the space between said base and said rear wall; and
 wherein said mechanical engagement includes toothed rack means disposed on said distal handle portion for engaging said pinion section to rotate said brush member in response to longitudinal motion of said handle.

43. The brush according to claim 38 wherein said toothed rack means comprises a rack extending longitudinally along said distal handle portion to rotate said pinion section and said brush member in a first rotary direction in response to distally directed motion of said handle relative to the brush head, and to rotate said pinion section and said brush member in a second rotary direction opposite to said first rotary direction in response to proximally direction motion of said handle relative to said brush head.

44. The brush according to claim 38 wherein said toothed rack means comprises first and second racks extending in spaced parallel relation along opposite diametric sides of said pinion section and at a small acute angle to the longitudinal dimension of said handle, said first and second racks being spaced sufficiently and positioned such that only said first rack operatively engages and rotate said pinion section during distally directed motion of said distal handle portion, and only said second rack operatively engages and rotates said pinion section during proximally directed motion of said handle portion, whereby both racks rotate the pinion section in the same rotation direction.

45. The brush according to claim 32 wherein said bristles in said first plurality of bristle tufts extend further from said first surface than do the bristles in said second plurality of bristle tufts.

46. The brush according to claim 32 wherein the bristles in said second plurality of bristle tufts are more flexible than the bristles in said first plurality of bristle tufts.

47. A method for applying rotational brush strokes to a surface in response to hand-powered longitudinally reciprocating motion of a handle mechanically engaged to a rotary brush in a brush head to rotate the rotary brush in response to the longitudinally reciprocating motion of the handle relative to the head, said method comprising the step of:
 positionally stabilizing the toothbrush head by urging positionally fixed tufts of bristles into frictional engagement with said surface so that the handle can be longitudinally reciprocated relative to the brush head.

* * * * *